United States Patent [19]

Newton et al.

[11] Patent Number: 5,124,357
[45] Date of Patent: Jun. 23, 1992

[54] CARNITINE SUPPLEMENTED FINISHING PIG DIET

[75] Inventors: G. Larry Newton, Tifton, Ga.; Stephen A. Blum, Des Moines, Iowa; Keith D. Haydon, Tifton, Ga.

[73] Assignees: University of Georgia Research Foundation, Inc., Athens, Ga.; Lonza Inc., Fair Lawn, N.J.

[21] Appl. No.: 766,901

[22] Filed: Sep. 26, 1991

Related U.S. Application Data

[63] Continuation of Ser. No. 387,856, Jul. 31, 1989, abandoned.

[51] Int. Cl.⁵ .................... A61K 35/78; A01N 37/30
[52] U.S. Cl. .......................... 514/554; 424/195.1; 514/557; 514/783; 426/807
[58] Field of Search ............... 424/549, 548, 442, 600, 424/195.1; 514/554, 557, 783; 426/807

[56] References Cited

U.S. PATENT DOCUMENTS 3,810,994  5/1974  Wiegand ........................ 424/316

OTHER PUBLICATIONS

"Nutrient Requirements of Swine", *Nutrient Requirements of Domestic Animals* No. 2, eighth revised edition (National Academy of Science, Washington, D.C. 1979).

G. L. Newton, et al., University of Georgia Swine Report (1986).

G. L. Newton, et al., University of Georgia Swine Report (1987).

*Primary Examiner*—Ronald W. Griffin
*Assistant Examiner*—R. Gitomer
*Attorney, Agent, or Firm*—Kilpatrick & Cody

[57] ABSTRACT

Feed compositions containing at least 0.6% lysine, preferably between about 0.7 and 0.8% lysine, and between approximately 0.1 to 400 ppm, preferably between 5 and 50 ppm, L-carnitine produce greater weight gains and feed efficiency, and alter fat metabolism, as compared with the same diet in the absence of the carnitine when fed to the finishing pigs. The L-carnitine can also be administered as a feed supplement providing between 0.05 and 15 mg L-carnitine/kg body weight/day, most preferably between 0.1 and 2.0 mg L-carnitine/kg body weight/day. The effect of the carnitine is sex linked, with significantly greater weight gains and feed efficiency observed for gilts than for barrows.

14 Claims, 1 Drawing Sheet

CARNITINE SUPPLEMENTED FINISHING PIG DIET

This is a continuation of copending application Ser. No. 07/387,856, filed o Jul. 31, 1989, now abandoned.

This generally relates to diet supplements for farm animals, especially pigs, for increasing weight gain and feed efficiency.

A major function of lipids in modern nutrition is to serve as a substrate for production of metabolic energy. Mechanisms regulating the production of metabolic energy under a wide variety of physiological conditions are required for survival of the species. The critical role of carnitine in the production of energy from long-chain fatty acids is well recognized. Carnitine also has a role in the production of metabolic energy from several substrates in addition to long-chain fatty acids. Thus, adequate carnitine status and carnitine nutriture are essential in maintaining health.

Unlike most vitamins and vitamin-like substances, carnitine was identified and synthesized long before the discovery of its nutritional role. Carnitine was first found in muscle extracts by two Russian scientists in 1905, identified as $\beta$-hydroxy-$\alpha$-butyrobetaine, and named from the latin carnis, meaning flesh or meat. In the late 1940's, Fraenkel discovered that carnitine was a necessary substance for the mealworm *Tenebrio molitor*. He named it vitamin $B_T$, although it was later established that carnitine is not a vitamin for higher organisms. Early research literature also calls carnitine vitamin $B_{11}$. In 1959, Fritz found that carnitine stimulated the rate of fat burning (called "beta-oxidation"). Subsequent investigations revealed the mechanism of carnitine's action: fats are transported by a carnitine-dependent mechanism into the mitochondria where they are burned for energy.

Carnitine is chemically termed 3-hydroxy-4-N-trimethylamino butyric acid; it is similar to choline and a close cousin to amino acids. Unlike amino acids, carnitine is not used for protein synthesis. Carnitine is not a vitamin since part of the animal requirement is fulfilled by biosynthesis. Carnitine, like many other biological molecules, comes in two forms: L-carnitine and D-carnitine. These isomers are mirror images of each other, much like the left hand is a mirror image of the right. Only the L-isomer is biologically active, however. The D-form is completely inactive, and may even inhibit the utilization of L-carnitine.

Whether supplied by the diet or from endogenous synthesis, carnitine is essential in the metabolism and movement of fatty acids within and between cells. An enzyme, carnitine acyltransferase, has been found to be part of the mechanism for releasing CoA and acyl-CoA. The effect of carnitine on fatty acid metabolism seems to be limited to fatty acids with chain lengths greater than $C_8$. Palmitylcarnitine also stimulates fat synthesis in livers so another vitamin role of carnitine may be in the regulation of lipogenesis.

Most organisms have the ability to produce their own carnitine. In 1980, Rebouche and Engel first demonstrated carnitine biosynthesis in humans. The endogenous production of carnitine appears to occur mainly in the liver, and requires two amino acids, lysine and methionine, three vitamins, vitamin $B_3$ (niacin), vitamin $B_6$ and vitamin C (ascorbic acid), and iron. Trimethyllysine is produced by methylation of lysine using a methyl group from methionine. The trimethyl-lysine is converted to an aldehyde using PALP as a co-factor, which is oxidized to a butyrate by an NAD-linked dehydrogenase. The butyrate is then hydroxylated by a ketoglutarate-ferrous ascorbate compound to form carnitine.

The role of carnitine in nutrition received little attention until 1973, when the first carnitine-deficient human patient was described. Since then, many clinical investigations have focused on biomedical aspects of carnitine deficiency, as well as on the effects of supplementary dietary carnitine on disease processes. No deficiency problems in normal vertebrates have yet been found under practical conditions. Nevertheless, young rats, chick embryos and rabbits on a low plane of nutrition have all been shown to grow more rapidly when carnitine has been supplied directly or indirectly.

One important, and as yet unresolved, issue is the relative contribution of diet and biosynthesis to the total carnitine intake. Some animal work, particularly studies conducted on adult animals, has been published in this area indicating that biosynthesis is far more important than diet.

G. L. Newton and K. D. Haydon reported in the 1986 University of Georgia Swine Report that feeding diets containing 0.95, 1.1 or 1.25% lysine, with or without 0.2% DL-carnitine HCl, to nursery pigs had an effect on daily weight gains and feed efficiency. Nursery, or starter, pigs are pigs that have been weaned between the ages of 21 to 28 days and weigh in the range of 10 to 15 pounds (4.8 to 5.2 up to 6.5 to 7 kg). Diet is 10 especially important in nursery pigs since the pigs have just been weaned and milk contains appreciable quantities of carnitine. It was postulated that supplementation of carnitine could reduce the lysine requirement, at least during some period following weaning.

The pigs were fed 72.4% corn and 24.2% soybean meal with vitamin, mineral and antibiotic supplementation. The 1.1% lysine diet produced high daily gains and greater feed efficiencies than the other diets. The effect on daily gain was significant throughout the study, while the effect on feed efficiency was significant for the first four days. There was also a significant linear and curvilinear effect of lysine level on feed efficiency after four and 28 days. Carnitine did not have a significant effect on performance and did not alter the need for lysine.

These results indicated the possibility of a greater response to supplemental lysine when nursery diets were also supplemented with carnitine. There were indications that post-weaning lag might be somewhat reduced in lighter weight pigs. The results of two supplemental trials conducted to determine if addition of carnitine to nursery diets would have an effect on post-weaning lag were reported in the 1987 University of Georgia Swine Report by G. L. Newton and K. D. Haydon. In the first trial, 144 pigs were fed simple corn-soy diets containing two levels of lysine and four levels of carnitine. For the other trial, 180 pigs were fed complex diets containing three levels of lysine and three levels of carnitine. When added to the simple diet, carnitine tended to produce an increase in feed intake during the first 4 days, which resulted in slightly better gains and feed efficiency at that time. When added to the complex diet, carnitine tended to increase food intake over the entire 20 day trial. Carnitine addition resulted in increased weight gains at 14 and 20 days.

The authors concluded that the effects of various levels of carnitine and the conditions under which carnitine addition to nursery diets may produce improved performance in pigs are still not completely understood, and that the effects appear to be related to lysine level, the age or size of the pig, and the level of intake rather than diet concentration.

Based on earlier studies showing that baby animals are deficient in carnitine biosynthesis, the effect of the carnitine in the nursery pigs, while significantly greater than predicted, was not unexpected. However, it is still not known if carnitine can have a significant effect on mature animals capable of synthesizing adequate levels of carnitine for the metabolism and storage.

It is therefore an object of the present invention to provide carnitine supplemented diets for altering fat metabolism and storage in animals capable of synthesizing carnitine.

It is a further object of the present invention to provide carnitine supplemented diets for increasing weight gain and feed efficiency in feeder animals, especially pigs between the weights of approximately 100 and 230 pounds.

SUMMARY OF THE INVENTION

Feed compositions containing at least 0.6% lysine, preferably between about 0.7 and 0.8% lysine, and between approximately 0.1 to 400 ppm, preferably between 5 and 50 ppm, L-carnitine produce greater weight gains and feed efficiency, and alter fat metabolism, as compared with the same diet in the absence of the carnitine when fed to finishing pigs. The effect of the carnitine is sex linked, with significantly greater weight gains and feed efficiency observed for gilts than for barrows.

The L-carnitine can also be administered as a feed supplement providing between 0.05 and 15 mg L-carnitine/kg body weight/day, most preferably between 0.1 and 2.0 mg L-carnitine/kg body weight/day.

Methods for formulation are also described. The diets can be optimized by conducting studies to determine the optimum amounts of amino acids, including lysine and methyl donors such as choline or methionine, to provide in conjunction with the L-carnitine based on the age, sex, weight, and breed of pigs to increase weight gains, feed efficiency, and tissue fat content.

DETAILED DESCRIPTION OF THE INVENTION

Figure 1:
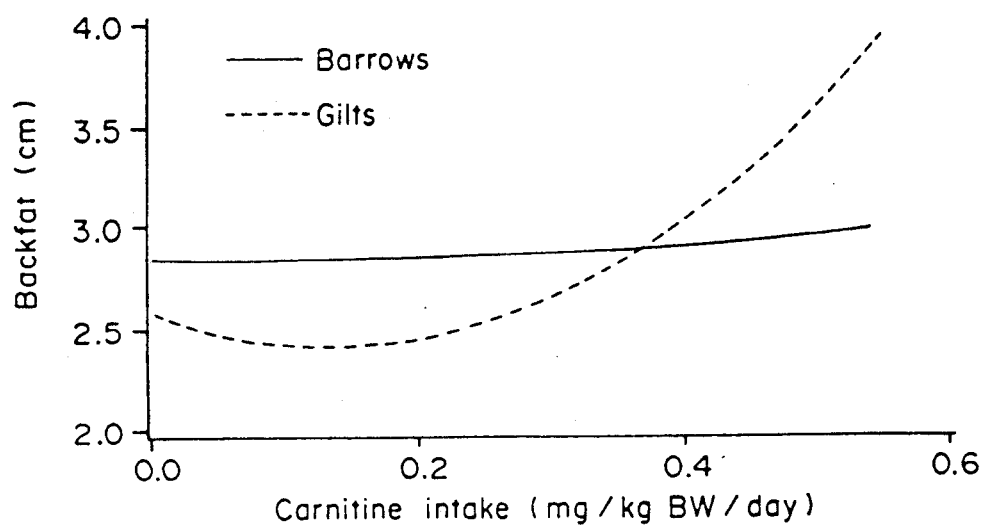
FIG. 1 is a graph of the effect of carnitine intake on backfat of barrows and gilts, backfat (cm) versus carnitine intake (mg/kg body weight/day).

Increased weight gain and feed efficiency can be achieved by supplementation of animal feeds containing minimum required levels of lysine with L-carnitine. The amount of required lysine and effective amount of L-carnitine is dependent on the age, sex, species, breed, and feed composition. Growth rate, feed conversion, and carcass composition are affected not only by nutrient intake, but also by breed, strain, sex and age. The criteria selected as indicative of a response to a particular diet or ingredient can influence requirements. For example, maximal carcass leanness may require greater concentrations of certain nutrients than maximal rate of gain. Lean pigs deposit more protein in their gain, which increases their requirements for protein and individual amino acids. Leanness is associated positively with feed efficiency; requirements for maximal feed efficiency are generally greater than those for maximal weight gain.

"Nutrient Requirements of Swine", *Nutrient Requirements of Domestic Animals* Number 2, eighth revised edition (National Academy of Science, Washington, D.C. 1979), provides extensive guidance in formulating diets for the feeding of swine. In the United States, most pigs are fed a diet consisting of approximately 97% corn and soybean with the remaining 3% consisting of carriers combined with one or more inorganic elements, vitamins, or antimicrobial compounds. For example, a standard diet may contain 79.5% corn; 17.4% soybean meal; 0.9% defluorinated phosphate; 0.65% limestone (35% Ca); 0.25% sodium chloride; 0.25% vitamin premix; 0.25% trace element premix; and 0.25% antimicrobial premix. Oats, sorghum and synthetic amino acids are sometimes added. In Europe, corn and soybean meal are generally not as available nor as cost effective as beans, peas, barley, wheat, rape seed meal, cassava (tapioca), molasses, fish, bone and meat meal. These materials do not yield as fast of a growth rate as soybean meal and corn.

In the United States, most swine producers wean piglets at approximately 21 to 28 days of age, at weights for crossbred piglets of about 10 pounds (4.8 to 5.2 kg) to 15 pounds (6.5 top 7 kg). Pigs between about two up to about three to four months of age, weighing between about 40 pounds (18 kg) and 110 pounds (50 kg), which are able to be maintained in non-temperature controlled environments, are called growing pigs. Finishing, or feeder, pigs are pigs being readied for market and range in weight and age from approximately greater than 110 pounds (50 kg) u to 220 pounds (100 kg) to 230 pounds (104 kg) and from greater than about four months up to approximately five to six months.

The dietary requirements for finishing pigs are quite different from nursery and growing pigs. Tables 5 and 6 of the Nutrient Requirements of Swine lists the amino acids, mineral elements, vitamins, and other dietary requirements for swine as a function of weight. For example, the lysine requirement for nursery pigs is from about 3.2 to 4.8 g daily, or from 1.25 to 0.95% of diet. The lysine requirement for finishing pigs ranges from approximately 12.2 to 17.1 g daily, or 0.61 to 0.57% of diet.

Carnitine is not listed as part of the daily nutritional requirements for swine. It was determined in the studies reported in 1986 and 1987 that the optimum amount of carnitine added to a diet for nursery pigs which was adequate in lysine was about 2000 ppm for a mixture of D- and L-carnitine, and about 800 ppm of L-carnitine. It has now been determined that diets containing from approximately 0.1 to 400 ppm, most preferably between 5 and 50 ppm, L-carnitine produce a significant increase in weight gain and feed efficiency in finishing pigs receiving a diet containing greater than 0.6% lysine, preferably about 0.7 to 0.8% lysine, an increase in the normal dietary amounts. Supplements may also be provided to the animals' normal diet to provide between 0.1 to 15 mg L-carnitine/kg body weight/daily, preferably between 0.1 and 2.0% L-carnitine. The amount of carnitine producing this effect is drastically less than the amount producing an effect in nursery pigs, even though the amount of lysine is decreased by a factor of less than one third.

The effect is sex dependent. As shown in the accompanying figures, described in more detail below, a much more dramatic effect of the carnitine administration is noted in gilts than in barrows. Gilts are leaner animals and therefore have a higher metabolic rate. The L-carnitine may therefore play a greater role in utilization of fatty acids for energy in gilts than in barrows.

The method for increasing feed efficiency and weight gain consists of providing lysine and L-carnitine levels in a feed composition to produce the maximum effect as a function of age and sex of the pigs. These amounts can be optimized for individual feed compositions or pig breeds by conducting studies of the nature described in the following examples. It is possible to optimize the diet to favorably alter the levels of fat in the tissue, based on these studies.

The effect of the combination of lysine and L-carnitine can also be optimized by adding additional sources of methyl groups for utilization in the conversion by the animal of lysine to carnitine. Examples of methyl donors known to those skilled in the art include methionine and choline. Choline would be administered at between 200 and 800 mg choline/kg.

The L-carnitine diets and supplements, and methods for utilization thereof, can be applied to other feeder animals such as feedlot cattle. Cattle are put into feedlots for between 90 and 120 days, usually 112 days, either shortly after weaning (at a weight of approximately 400 to 500 pounds) or more typically, after a second summer on grass (at a weight of between 700 and 900 pounds). The latter group are considered analogous to finishing pigs.

The present invention will be further understood with reference to the following non-limiting examples.

EXAMPLE 1

Administration of L-lysine and L-carnitine to finishing pigs

Forty-two finishing pigs, 21 barrows and 21 gilts, average weight 74.6 kg, were provided with corn-soy diets containing 0.6% lysine and either 0, 5 or 10 ppm added L-carnitine. The pigs were individually housed and fed, and were removed from test after 35 days. The average weight of the pigs was 106.7 kg. The diet for the finishing pigs fed supplemental L-carnitine consisted of:

| Item | Basal diet* |
| --- | --- |
| Ground corn | 84.86 |
| Soybean meal | 12.59 |
| Defluorinated phosphate | 1.18 |
| Ground limestone | .47 |
| Salt | .35 |
| Vitamin premix | .20 |
| Trace mineral premix | .10 |
| Antibiotic | .25 |

*This diet was supplemented with either 0, 5, or 10 mg/kg of L-carnitine.

During the first 14 days pigs fed 5 ppm carnitine consumed less ($p<0.05$) feed than pigs fed the control diet (3.01 vs 3.33 kg/pig/day), but there were no significant differences for weight gain or feed efficiency. During the second 14-day period there was an interaction ($p<0.05$) between dietary carnitine and sex of pig for feed intake. Barrows fed the 10 ppm diet consumed more feed than barrows on other diets (3.96, 3.41 and 3.42 kg/pig/day for 10 ppm, 5 ppm and control diets, respectively) while gilts consumed slightly less (2.94, 3.11 and 3.14 kg/pig/day for 10 ppm, 5 ppm and control diets, respectively). Over the trial, there were differences in gain (0.83, 0.86 and 0.84 kg/day for pigs on a control diet or receiving 5 ppm and 10 ppm L-carnitine, respectively), feed intake (3.38, 3.30 and 3.35 kg/day for control, 5 ppm and 10 ppm L-carnitine, respectively), feed/gain (4.11, 3.92 and 4.04 for control, 5 ppm and 10 ppm L-carnitine, respectively) and backfat (2.73, 2.69 and 2.76 for control, 5 ppm and 10 ppm L-carnitine, respectively) due to carnitine supplementation. In general, pigs fed L-carnitine consumed less feed and grew more slowly near the beginning of the trial and grew faster on the same amount of feed during the last 14 days of the trial, compared to pigs fed the control diet.

EXAMPLE 2

Administration of L-lysine and L-carnitine to a second group of finishing pigs, results analyzed to determine effect of sex A second group of forty-two finishing pigs, 21 barrows and 21 gilts, average weight 75.9 kg, were provided with corn-soy diets containing 0.6% lysine and either 0, 5 or 10 ppm added L-carnitine. The pigs were individually housed and fed, and were removed from test after 28 days. The average weight of the pigs was 102.5 kg. The diet was as described in example 1.

The initial weights for the three groups were initially the same. Over the first fourteen days, the daily gain, in kg, was 1.04, 0.89, and 0.98 for 0, 5, and 10 ppm L-carnitine, respectively. The daily feed, in kg, was 3.53, 3.27, and 3.59 for 0, 5, and 10 ppm L-carnitine, respectively. The gain/feed ratio was 0.29, 0.25, and 0.27 for 0, 5, and 10 ppm L-carnitine, respectively.

Performance was then compared after an additional fourteen days (total of 28 days). The final weight for the three groups was 102.5, 102.1, and 101.8, for 0, 5 and 10 ppm L-carnitine, respectively. Daily gain for the second fourteen days, in kg, was 0.91, 0.96, and 0.91 for 0, 5, and 10 ppm L-carnitine, respectively. Daily gain for the entire 28 days, in kg, was 0.97, 0.93, and 0.95 for 0, 5, and 10 ppm L-carnitine, respectively. Daily feed for the second fourteen days, in kg, was 3.28, 3.36, and 3.57 for 0, 5, and 10 ppm L-carnitine, respectively. Daily feed for the entire 28 days, in kg, was 3.36, 3.22, and 3.42, for 0, 5, and 10 ppm L-carnitine, respectively. Gain/feed ratio for the second fourteen days was 0.28, 0.28 and 0.27 for 0, 5, and 10 ppm L-carnitine, respectively. Gain/feed ratio for the entire 28 days was 0.27, 0.27, and 0.26, for 0, 5, and 10 ppm L-carnitine, respectively. The backfat levels, in cm, for the entire 28 days, was 2.71, 2.64, and 2.99 for 0, 5, and 10 ppm L-carnitine, respectively. These differences are statistically significant at $p<0.05$.

When data from the two trials was combined, the initial observations were reinforced. Over the first fourteen days, the daily gain, in kg, was 0.92, 0.80, and 0.87 for pigs fed 0, 5, and 10 ppm L-carnitine, respectively. The daily feed, in kg, was 3.43, 3.14, and 3.33. These differences are statistically significant at $p<0.05$. The gain/feed ratio was 0.27, 0.24, and 0.26 for pigs fed 0, 5 and 10 ppm L-carnitine, respectively.

When the effect of dietary carnitine on feed consumption over the first fourteen days was analyzed on the basis of sex, the differences were statistically significant at $p<0.10$. Daily feed, in kg, was 3.51, 3.33, and 3.47 for barrows, and 3.36, 2.94, and 3.17 for gilts, for 0, 5, and 10 ppm L-carnitine, respectively.

Figure 2:
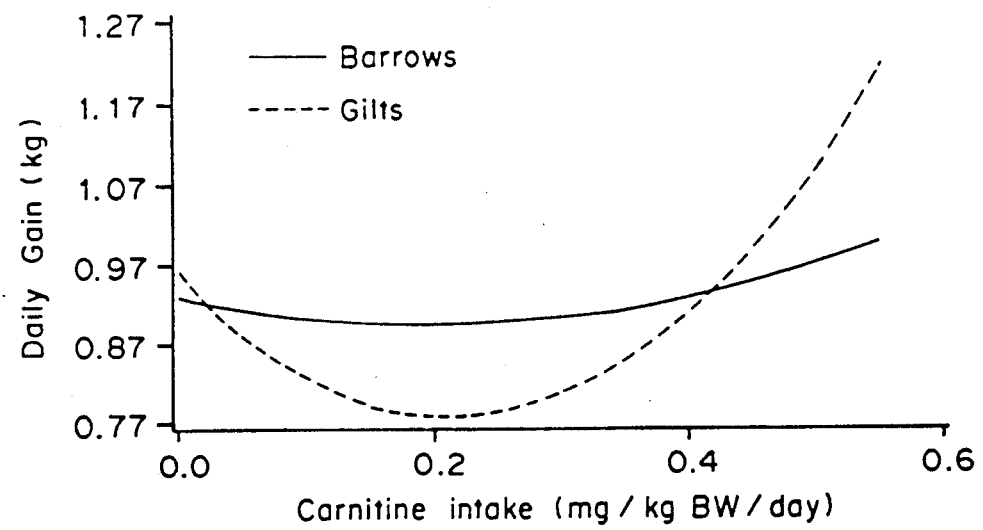
FIG. 2 is graph of the effect of carnitine intake on weight gain of barrows and gilts, daily gain (kg) versus carnitine intake (mg/kg body weight/day).

The effect of pig sex and dietary carnitine on feed consumption after 28 days was as follows. Daily feed, in kg, for barrows fed 0, 5, and 10 ppm L-carnitine, was 3.44, 3.42, and 3.67, respectively. Daily feed, in kg, for gilts fed 0, 5 and 10 ppm L-carnitine, was 3.27, 3.02, and 3.12, respectively. The effect by sex of the different levels of carnitine on backfat is shown in FIG. 1. The effect by sex of the different levels of L-carnitine on daily gain is shown in FIG. 2. Gilts exhibit a pronounced curvilinear response in both backfat and daily gain in response to supplementary L-carnitine. It is therefore possible, by varying the levels of L-carnitine administered to pigs of different ages and sexes to alter the amount of fat in the tissue.

Modifications and variations of the present invention, feed compositions and methods for formulation and administration thereof to finishing pigs, will be obvious to those skilled in the art from the foregoing detailed description. Such modifications and variations are intended to come within the scope of the amended claims.

We claim:

1. A feed for finishing pigs greater than four months of age comprising between approximately 0.6% and less than 0.95% lysine and between approximately 0.1 and 400 ppm L-carnitine.

2. The feed composition of claim 1 comprising between approximately 0.6 and 0.8% lysine and between approximately 5 and 50 ppm L-carnitine.

3. The feed composition of claim 1 further comprising materials selected from the group consisting of corn, soybean meal, oats, sorghum, molasses, synthetic amino acids, beans, peas, barley, wheat, rape seed meal, cassava, fish meal, bone meal, meat meal, vitamins, antibiotics, and trace elements.

4. The feed composition of claim 1 further comprising methyl donors selected from the group consisting of methionine and choline.

5. A method for increasing weight gain and feed utilization in finishing pigs comprising providing thereto between approximately 0.05 and 15 mg L-carnitine/kg body weight/day to said finishing pigs in combination with a feed containing between approximately 0.6% and less than 0.95% lysine.

6. The method of claim 5 wherein between approximately 0.1 and 2.0 mg L-carnitine/kg body weight/day is provided to finishing pigs.

7. The method of claim 6 wherein the diet contains between approximately 0.6 and 0.8% lysine and between approximately 5 and 50 ppm L-carnitine, to provide between approximately 0.1 and 2.0 mg L-carnitine/kg body weight.

8. The method of claim 6 comprising providing materials selected from the group consisting of corn, soybean meal, oats, sorghum, molasses, synthetic amino acids, beans, peas, barley, wheat, rape seed meal, cassava, fish meal, bone meal, meat meal, vitamins, antibiotics, and trace elements.

9. The method of claim 5 further comprising in the feed methyl donors selected from the group consisting of methionine and choline.

10. The method of claim 5 further comprising providing in the feed an amount of L-carnitine effective for producing an increase in weight gain and feed efficiency in gilts.

11. The method of claim 5 further comprising providing in the feed an amount of L-carnitine effective for producing an increase in weight gain and feed efficiency in barrows.

12. The method of claim 5 further comprising providing in the feed an amount of L-carnitine effective in altering the fat content of the tissues in finishing pigs.

13. A method for supplementing a feed composition for finishing pigs greater than four months of age comprising providing therein between approximately 0.1 and 400 ppm L-carnitine in combination with between approximately 0.6% and less than 0.95% lysine.

14. The method of claim 13 comprising providing in the feed between approximately 0.6 and 0.8% lysine and between approximately 5 and 50 ppm L-carnitine.

* * * * *